(12) United States Patent
Schneider

(10) Patent No.: US 9,771,680 B2
(45) Date of Patent: Sep. 26, 2017

(54) METHOD OF CHARACTERIZING AN ARTICLE MADE OF COMPOSITE MATERIAL

(71) Applicant: SNECMA, Paris (FR)

(72) Inventor: Julien Schneider, Corbeil-Essonnes (FR)

(73) Assignee: SNECMA, Paris (FR)

( * ) Notice: Subject to any disclaimer, the term of this patent is extended or adjusted under 35 U.S.C. 154(b) by 352 days.

(21) Appl. No.: 14/419,709

(22) PCT Filed: Jul. 31, 2013

(86) PCT No.: PCT/FR2013/051851
§ 371 (c)(1),
(2) Date: Feb. 5, 2015

(87) PCT Pub. No.: WO2014/023893
PCT Pub. Date: Feb. 13, 2014

(65) Prior Publication Data
US 2015/0212013 A1    Jul. 30, 2015

(30) Foreign Application Priority Data

Aug. 7, 2012 (FR) .................... 12 57670

(51) Int. Cl.
*D06H 3/08* (2006.01)
*G01N 23/18* (2006.01)
(Continued)

(52) U.S. Cl.
CPC .............. *D06H 3/08* (2013.01); *D01H 13/26* (2013.01); *G01N 23/046* (2013.01); *G06T 7/0004* (2013.01); *G06T 7/269* (2017.01); *D01G 31/006* (2013.01); *D06H 2201/10* (2013.01); *G01N 23/18* (2013.01); *G01N 2223/419* (2013.01); *G06T 2207/30124* (2013.01)

(58) Field of Classification Search
CPC ................ G01N 23/046; G01N 23/18; G01N 2223/419; G01N 2223/60; G01N 2223/611; G01N 2223/615; D06H 3/08; D06H 2201/00; D06H 2201/10; D01G 31/003; D01G 31/006; D01H 13/26; G06T 7/0004; G06T 7/269; G06T 2207/30108; G06T 2207/30124
See application file for complete search history.

(56) References Cited

U.S. PATENT DOCUMENTS

2011/0274369 A1    11/2011    Smith et al.

OTHER PUBLICATIONS

International Search Report issued Sep. 26, 2013 in PCT/FR2013/051851 Filed Jul. 31, 2013.
(Continued)

*Primary Examiner* — Anastasia Midkiff
(74) *Attorney, Agent, or Firm* — Oblon, McClelland, Maier & Neustadt, L.L.P.

(57) ABSTRACT

A characterization method for characterizing an article made of composite material having woven, braided, or sewn fiber reinforcement, the method including a determination step of using X-ray tomography to determine gray levels of at least a portion of the article, followed by an exploitation step of exploiting the gray levels to obtain information concerning the weaving by distinguishing between at least the free matrix and the threads of fibers mixed with the matrix, the threads being considered as being a material that is homogeneous.

13 Claims, 3 Drawing Sheets

(51) Int. Cl.
    *G06T 7/00*       (2017.01)
    *D01G 31/00*    (2006.01)
    *D01H 13/26*    (2006.01)
    *G06T 7/269*    (2017.01)
    *G01N 23/04*    (2006.01)

(56) References Cited

OTHER PUBLICATIONS

Ivo Babuska, et al., "Damage analysis of fiber composites; Part I: Statistical analysis on fiber scale", Computer Methods in Applied Mechanics and Engineering, vol. 172, No. 1-4, XP002695948, Apr. 1999, pp. 27-77.

D. Tsarouchas, et al., "Extraction of fibre network architecture by X-ray tomography and prediction of elastic properties using an affine analytical model", Acta Materialia, vol. 59, No. 18, XP028295643, Jul. 2011, pp. 6989-7002.

G. Moldovan, et al., "Noise deconvolution for area fraction measurements", Materials Science and Technology, vol. 20, No. 1, XP009168685, Jan. 2004, pp. 16-20.

METHOD OF CHARACTERIZING AN ARTICLE MADE OF COMPOSITE MATERIAL

TECHNICAL FIELD AND PRIOR ART

The invention lies in the field of methods of characterizing materials and structures for use in engineering industry in general, and in the aviation industry in particular.

The invention applies to composite materials having fiber reinforcement that is woven, braided, or indeed sewn, which materials find numerous applications in the field of constructing parts for airplanes, and particularly but not exclusively parts for aeroengines, e.g. fan blades. These materials present properties that are advantageous in terms of weight, strength, and ease of fabricating the parts.

For a given part, it is useful to have knowledge about the characteristics of the fiber reinforcement in the part in order to improve knowledge about its mechanical properties. The fiber reinforcement is generally described using weaving parameters, such as fiber fraction ($V_f$), the distances between weaving columns ($d_c$ for warp yarns and $d_t$ for weft yarns), the ratio between the quantities of warp yarns and weft yarns (warp/weft ratio), and contraction ($\theta$).

These characteristics can vary within a single given part, depending on the shape of the part. It is thus useful to be able to determine how these characteristics vary over the entire volume of the part.

Various techniques are known for performing characterization, and they are discussed herein where they concern composite materials having matrix that is organic. These characterization techniques make use either of chemical dissolution and weight measurements, or else of making cuts and taking measurements on section planes.

Certain kinds of information can thus be obtained, such as fiber fraction, which may be determined by weighing after dissolving away the matrix by chemical etching with acid, and also concerning distances between columns, which are measured by making observations on a section.

However other parameters remain difficult to extract: thus, it is difficult to ensure that a section plane follows all of the threads in a given weaving column, so it is particularly difficult to measure contraction and waviness, in particular over a volume representative of a weaving cell having a large quantity of threads (which may be greater than 100 in certain weaves). Likewise, the warp/weft ratio can be obtained only indirectly.

In addition to providing only incomplete characterization, those techniques have the major drawbacks of being techniques that are destructive, and of being applicable to small volumes only of the material (generally 4 grams (g)), and of being expensive in terms of the time required to perform them. Dissolving material also gives rise to problems of potential errors in the measurements due to possible impurities (which risk increases with increasing volume under study) and they give rise to waste that is difficult to recycle.

The invention seeks to resolve the above-mentioned difficulties.

DEFINITION OF THE INVENTION—ADVANTAGES IT PROVIDES

The invention consists in a characterization method for characterizing an article made of composite material having woven, braided, or sewn fiber reinforcement, the method comprising a determination step of using X-ray tomography to determine gray levels of at least a portion of the article, followed by an exploitation step of exploiting said gray levels to obtain information concerning the weaving by distinguishing between at least the free matrix and the threads of fibers mixed with the matrix, said threads being considered as being a material that is homogeneous.

Because of these characteristics, the article is characterized in a manner that is not destructive, and access is obtained quickly and with great accuracy to information that has previously been very difficult to obtain. This constitutes a significant advance, since work is done on an intermediate scale by considering that the threads of fibers mixed with the matrix as a homogeneous material have gray levels that can be distinguished from the gray levels of the matrix.

This methodology also makes it possible to work on samples of large size.

Advantageously, the determination step is performed with the article rotating about an axis parallel to a fiber direction of the sample of material, and the exploitation step is performed by distinguishing weft threads and warp threads from the free matrix.

This constitutes a method based on a very innovative phenomenon that has only recently been characterized and that makes it possible to determine accurately parameters that have previously been difficult or impossible to access. It is only by performing studies of optimized parameters that has made it possible to detect the existence of the phenomenon, whereby the warp threads and the weft threads, each being considered as a homogeneous material, present respective different distributions of gray levels.

In an implementation, the exploitation step comprises determining a distribution of gray levels, and then deconvoluting at least two Gaussian curves in said distribution in order to determine at least a thread volume fraction. This makes it possible to obtain information concerning a section or a volume of the article. The exploitation step may also be performed with the help of a predetermined relationship between the fiber fraction in the material and the thread volume fraction. The exploitation step may in particular comprise deconvoluting at least three Gaussian curves in order to determine the volume fractions of the weft threads and of the warp threads, and a weft/warp ratio between the quantities of weft yarn fibers and of warp yarn fibers, which is very advantageous since this information is difficult to obtain otherwise.

In a particular version of the invention, the exploitation step comprises determining gray level distributions for a succession of sections of the article, and obtaining a distance between weaving columns by applying a Fourier transform or by measuring peak-to-peak distances in the succession of sections.

In another implementation, the exploitation step comprises displaying threads in an image of the article as a function of gray levels. Preferably, the warp yarns and the weft yarns are distinguished within the image as a function of gray levels, and if necessary, a contraction angle or a waviness parameter of a thread is determined, which is very advantageous, since this information is very difficult to obtain otherwise.

The invention is particularly applicable to a composite material having woven fiber reinforcement constituted by fibers made of carbon or of some other material. The material may have a matrix that is organic, metallic, or ceramic. The article under study may be a part for a turbojet, and advantageously it may be a complete structure. It could also be a sample.

DESCRIPTION OF IMPLEMENTATIONS

Figure 1:
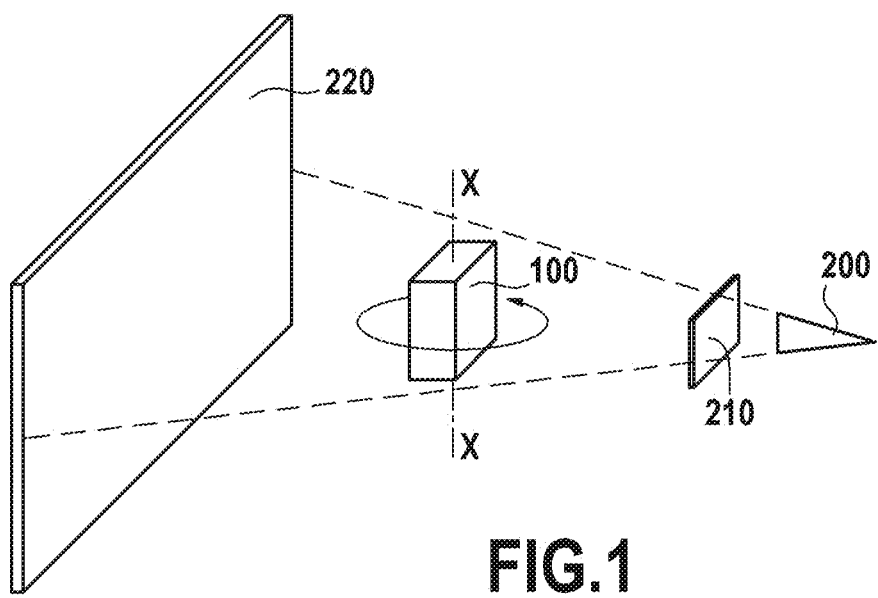
FIGS. 1 and 2 show a first implementation of a method of the invention.

FIG. 1 shows a first implementation of the invention. More precisely, a device for X-ray tomography study is shown. Specifically, the device is a micro computed tomography (μ-CT) device. It is applied to characterizing an article 100 made of composite material having an epoxy organic matrix and carbon fibers. The carbon fibers have a diameter of about 5 micrometers (μm) and they are not visualized in the method described.

The study device has an X-ray source 200, a filter 210 for filtering the source beam, e.g. by using a piece of copper that is 0.1 millimeter (mm) thick, and a two-dimensional (2D) detector 220. The article 100 is positioned between the filter 210 and the detector 220, in the beam of X-rays. It rotates about an axis X relative to the detector 220 and the filter 210. The tomography appliance records the gray levels of the voxels of the article 100.

Figure 2:
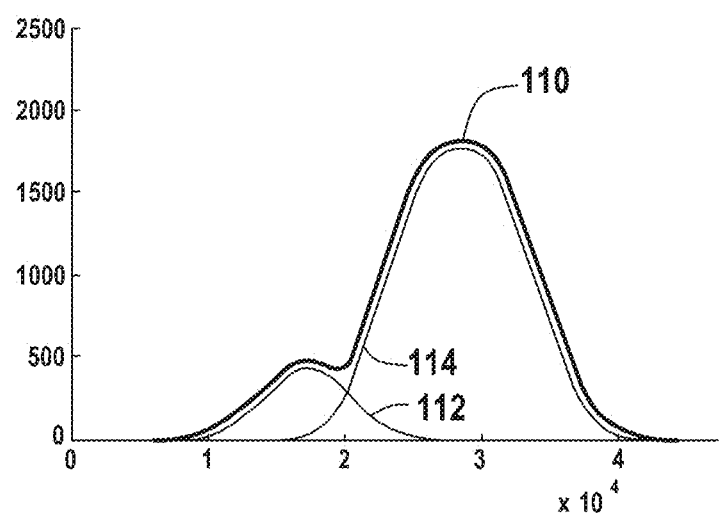

FIG. 2 is a graph plotting the curve 110 representing the distribution of gray levels throughout the volume of the article 100. The abscissa axis indicates gray level (from 1 to $2^{16}-1=65535$), and the scale on the ordinate axis gives the number of voxels having a given gray level.

The distribution curve 110 presents two visible maxima. In certain circumstances, the curve presents three maxima, as described below with reference to FIGS. 3 and 4.

Thereafter, when analyzing this curve 110, it is considered that the composite material is constituted by a free matrix and by threads of fibers mixed with the matrix, the threads being considered as constituting a material that is homogenous.

The curve is deconvoluted to obtain two Gaussian curves, relying on the fact that each of these two homogenous materials has a respective distribution of gray levels that is Gaussian. Thus, the curve 110 is caused to reveal the respective contributions from the epoxy matrix and from the threads. These two contributions are Gaussian curves having references 112 and 114. In this example, the threads have a greater contribution and higher gray levels.

By summing the numbers of voxels in each of the two Gaussian curves 112 and 114, it is possible to obtain the volume occupied by the matrix and the volume occupied by the threads, and by taking the ratio, it is possible to obtain the thread volume fraction, written $V_{thread}$, in the volume under study of the article 100.

Figure 3:
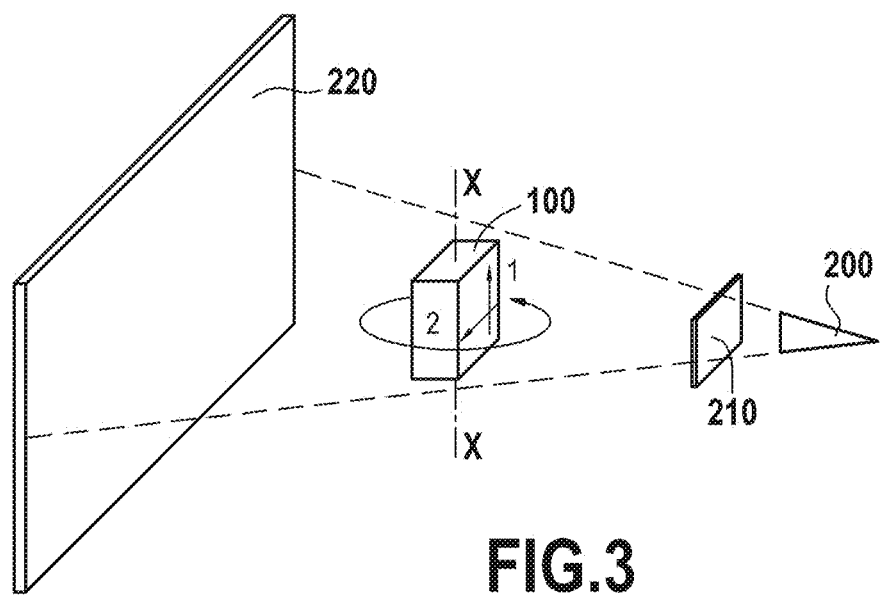
FIGS. 3 and 4 show a second implementation of a method of the invention.

FIG. 3 shows a second implementation. It differs from the first implementation in two aspects.

Firstly, the article 100 is positioned with one of its weaving directions parallel to the axis of rotation X. This weaving direction is referenced 1 in the figure. The direction 2 is perpendicular to the axis X.

Secondly, the X-ray source 200 is optimized by applying high current and low voltage for generating the X-rays.

The tomography appliance records the gray levels of the voxels in the article 100, as in FIG. 1.

Figure 4:
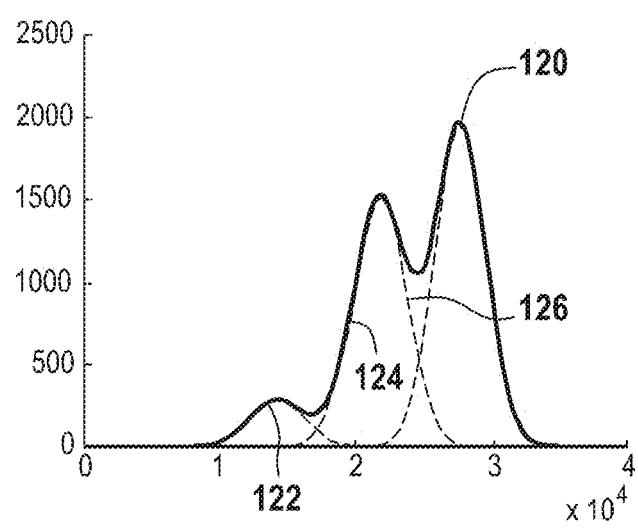

FIG. 4 is a graph plotting the curve 120 representing the distribution of gray levels throughout the volume of the article 100 in the second implementation. Once more, the abscissa axis gives the gray level and the ordinate axis gives the number of voxels presenting a given gray level.

The distribution curve 110 shows three visible maxima.

Possible causes for this phenomenon appear to be the orthotropic nature of carbon fiber, and/or the fact that the gaps between the fibers within the threads possess a predefined orientation. Furthermore, these two phenomena may be coupled.

In any event, it can be seen that the threads present levels of absorption that are different in their transverse direction and in their longitudinal direction.

In the arrangement of FIG. 3, all of the threads of direction 1 always pass X-rays transversely, whereas the threads of direction 2 sometimes pass X-rays longitudinally during rotations of the article 100 about the axis of rotation X. The gray levels of the threads of direction 1 (parallel to the axis of rotation) are lower than the gray levels of the threads of direction 2.

The curve is deconvoluted into three Gaussian curves, relying on the fact that the matrix, the threads of direction 1, and the threads of direction 2 have respective distributions of gray levels that are Gaussian.

The threads of direction 1 and the threads of direction 2 are considered as being respective homogeneous materials.

Thus, the curve 120 can reveal the respective contributions of the epoxy matrix, of the threads of direction 1, and of the threads of direction 2 (or the weft threads and the warp threads). These three contributions are Gaussian curves given references 122, 124, and 126. In this example, the threads of direction 2 have the greatest contribution. Both types of thread have gray levels that are higher than the matrix.

By summing the numbers of voxels in each of the three Gaussian curves 122, 124, and 126, it is possible to obtain the volume occupied by the matrix, the volume occupied by the weft threads, and the volume occupied by the warp threads, and by taking ratios, it is possible to obtain the thread volume fraction $V_{thread}$ in the volume under study of the article 100 with greater accuracy than when using the method of FIGS. 1 and 2, and it is also possible to obtain the ratio between the warp threads and the weft threads (warp/weft ratio).

A prior study of reference homogeneous samples made of composite material comprising an epoxy matrix and carbon fibers at different fiber fractions in the material has been undertaken. That study comprised using tomography and deconvolution as described with reference to FIGS. 1 and 2 (or FIGS. 3 and 4), and also dissolving the samples in order to determine their fiber fractions. Thus, for those reference samples, the overall fiber fractions $V_f$ in the material are known as are the fiber fractions in the threads.

The inventors have found in particular that the fiber fractions in the threads are proportional to the fiber fractions $V_f$ in the material over a range of fiber fractions $V_f$ in the material extending from 54% to 64%.

In that range where the relationship is linear, and also outside that range, the prior study makes it possible, for a volume under study of a given article 100, to deduce the overall fiber fraction $V_f$ from the thread fraction as obtained by the study using tomography and deconvolution.

Figure 5:
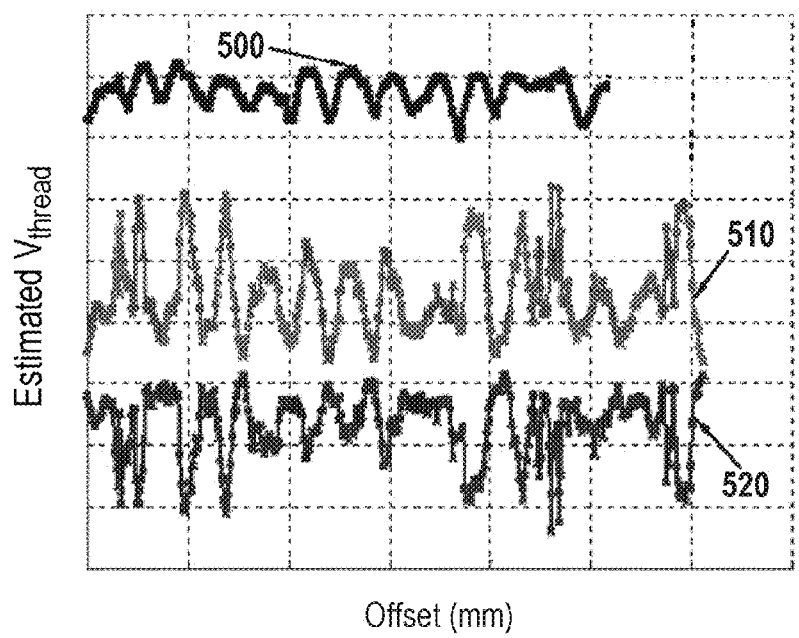
FIG. 5 shows results obtained in the context of a variant of the implementation of FIGS. 3 and 4.

FIG. 5 shows the appearance of a variant of the implementation of FIGS. 3 and 4. Instead of studying the distribution of gray levels throughout the volume of the article 100, such a distribution is studied for each section (or subvolume of small thickness) of the volume of the article as can be visualized using the tomography system. The sections are identified by the values of their offsets along an axis, which values are plotted along the abscissa axis in FIG. 5, being graduated in millimeters, for an article having a dimension of 3 centimeters (cm).

For each section, the curve is deconvoluted into three Gaussian curves. Thus, the respective contributions of the epoxy matrix and of the weft threads and of the warp threads are revealed in the curve 110. The thread volume fraction $V_{thread}$ in the section under study is obtained, which is represented in the form of a curve 500, together with the weft thread and warp thread volume fractions which are represented by curves 510 and 520.

From the curves 500, 510, and 520, it is possible to extract the distances between the warp columns $d_c$ and between the weft columns $d_t$. When these parameters are constant, this can be done by a Fourier transform so as to determine the frequency of the undulations (or "waves") in the curves 500, 510, and/or 520. If the distances between columns are not constant, information can be obtained by measuring the distances between peaks in the curves 500, 510, and 520.

Figure 6:
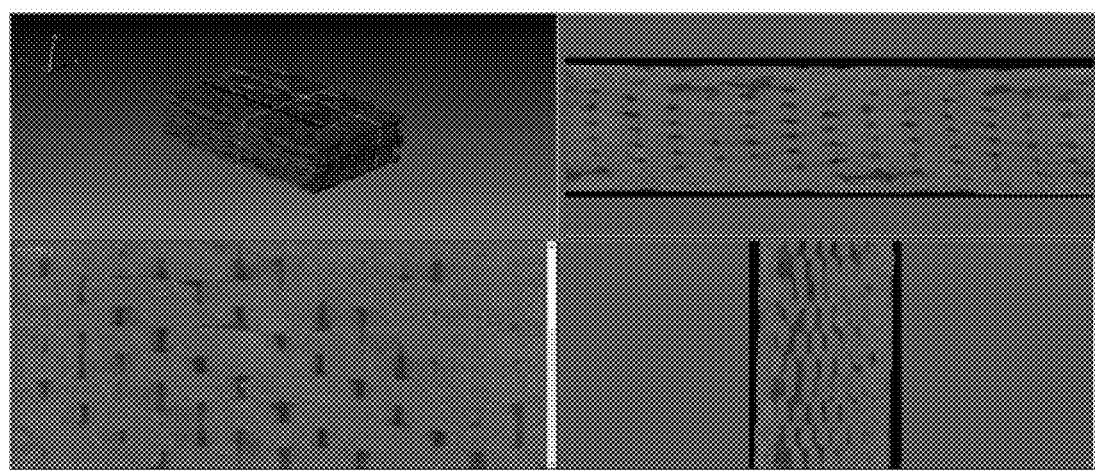
FIG. 6 shows a third implementation of the invention.

FIG. 6 shows a third implementation of the invention. This involves three-dimensional (3D) imaging of the volume of the article 300 by displaying, e.g. using selected colors, voxels having gray levels within a range defined by one or two thresholds as a function of the values expected for the matrix, and for the threads, or possibly when using the setup of FIG. 3, for the weft threads or for the warp threads. It is thus possible to follow a given thread accurately in the image, and thus to determine its parameters for contraction (θ) and waviness.

In a variant, images are acquired with the article 300 positioned in such a manner that the warp threads and the weft threads are oriented at 45° relative to the axis of rotation. The warp and weft threads thus pass X-rays on average in the same manner over a complete rotation. Only two Gaussian curves appear, as in FIG. 2.

In another variant, the axis of rotation is aligned with the direction perpendicular to the weaving plane (perpendicularly to the warp and weft threads), and once more these warp and weft threads pass X-rays on average in the same manner over a complete rotation. Only two Gaussian curves appear, as in FIG. 2.

The invention is advantageously applied to complete structures made of composite material for aviation applications, and in particular to aeroengine parts, such as a blade or a casing that can be studied as a whole without previously cutting off a sample.

The invention is not limited to the implementations described, but extends to any variant coming within the limits of the scope of the claims.

The invention claimed is:

1. A characterization method for characterizing an article made of composite material having woven, braided, or sewn fiber reinforcement, the method comprising:
   a determination step of using X-ray tomography to determine gray levels of at least a portion of the article: and
   an exploitation step of exploiting said gray levels to obtain information concerning the article by distinguishing between at least a free matrix and threads of fibers mixed with the matrix, said threads being considered as being a material that is homogeneous.

2. A characterization method according to claim 1, wherein the determination step is performed with the article rotating about an axis parallel to a fiber direction of the article, and the exploitation step is performed by distinguishing weft threads and warp threads from the free matrix.

3. A characterization method according to claim 1, wherein the exploitation step comprises determining a distribution of gray levels, and deconvoluting at least two Gaussian curves in said distribution in order to determine a thread volume fraction.

4. A characterization method according to claim 3, wherein the exploitation step is performed using a predetermined relationship between a fiber fraction in the material and the thread volume fraction.

5. A characterization method according to claim 4, wherein the exploitation step comprises deconvoluting at least three Gaussian curves in order to determine volume fractions of the weft threads and of the warp threads, and a weft/warp ratio between the quantities of weft yarn fibers and of warp yarn fibers.

6. A characterization method according to claim 5, wherein the exploitation step comprises determining gray level distributions for a succession of sections of the article, and obtaining a distance between weaving columns by applying a Fourier transform or by measuring peak-to-peak distances in the succession of sections.

7. A characterization method according to claim 6, wherein the exploitation step comprises displaying threads in an image of the article as a function of gray levels.

8. A characterization method according to claim 7, wherein the warp yarns and the weft yarns are distinguished within the image as a function of gray levels.

9. A characterization method according to claim 8, wherein a contraction angle or a waviness parameter of a thread is determined.

10. A characterization method according to claim 1, wherein the fiber reinforcement is woven and constituted by fibers made of carbon.

11. A characterization method according to claim 1, wherein the material has a matrix that is organic, metallic, or ceramic.

12. A characterization method according to claim 1, wherein the article is a part for a turbojet.

13. A characterization method according to claim 1, wherein the article is a complete structure or a sample.

* * * * *